United States Patent [19]

Vogt et al.

[11] 4,282,226
[45] Aug. 4, 1981

[54] THIOXOPYRAZOLO[1,5-C]QUINAZOLINE DERIVATIVES, ANTI-ALLERGIC COMPOSITIONS AND METHODS FOR TREATING ALLERGIC CONDITIONS BY PARENTERAL ADMINISTRATION, AEROSOL OR INSUFFLATION

[75] Inventors: B. Richard Vogt, Yardley, Pa.; Ligaya G. Magbanua, Allentown, N.J.

[73] Assignee: E. R. Squibb & Sons, Inc., Princeton, N.J.

[21] Appl. No.: 148,433

[22] Filed: May 9, 1980

Related U.S. Application Data

[63] Continuation-in-part of Ser. No. 900,050, Apr. 26, 1978, abandoned.

[51] Int. Cl.$^3$ .................. A61K 31/505; C07D 487/04
[52] U.S. Cl. ..................................... 424/251; 544/250
[58] Field of Search ....................... 544/250; 424/251

[56] References Cited

U.S. PATENT DOCUMENTS

| | | | |
|---|---|---|---|
| 3,313,815 | 4/1967 | Wolfe et al. | 544/250 |
| 3,531,482 | 9/1970 | Ott | 544/250 X |
| 3,895,027 | 7/1975 | Katner | 544/250 X |
| 3,897,434 | 7/1975 | Katner | 544/250 |
| 3,899,508 | 8/1975 | Wikel | 544/250 X |
| 3,903,106 | 9/1975 | Katner et al. | 544/250 X |
| 4,048,168 | 9/1977 | Yamamoto | 424/251 X |
| 4,076,818 | 2/1978 | Vogt | 424/251 |
| 4,145,420 | 3/1979 | Vogt | 544/250 X |

FOREIGN PATENT DOCUMENTS 1042299 9/1966 United Kingdom .................... 544/250

OTHER PUBLICATIONS

Medicinal Chemistry, 3rd ed., part I, Burger, ed., Wiley-Interscience, New York, 1970, pp. 64–80, 131, 160.
Medicinal Chemistry, 3rd ed., part II, Burger, ed., Wiley-Interscience, New York, 1970, pp. 1371–1372, 1383–1385.
Organic Chemistry of Sulfur, Oae, ed., Plenum Press, New York, pp. 26–32, 189–229.
Malen et al., J. Med. Chem., vol. 14, No. 3, pp. 244–246, (1971).
Srivastava et al., J. Med. Chem., vol. 20, No. 2, pp. 256–261, (1977).
Beattie et al., J. Med. Chem., vol. 20, No. 5, pp. 714–721, (1977).
Chavdarian et al., J. Med. Chem., vol. 22, No. 11, pp. 1317–1322, (1979).
Walker et al., J. Med. Chem., vol. 21, No. 12, pp. 1335–1338, (1978).
Berkowitz et al., J. Med. Chem., vol. 20, No. 1, pp. 134–137, (1977).
Hull et al., Chemical Abstracts, vol. 84, 180164x, (1976).

*Primary Examiner*—Donald G. Daus
*Assistant Examiner*—Diana G. Rivers
*Attorney, Agent, or Firm*—Lawrence S. Levinson; Burton Rodney

[57] ABSTRACT

Compounds are provided having the structure

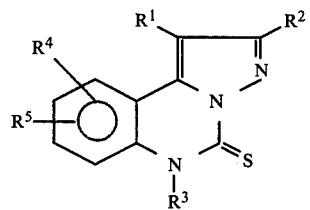

wherein $R^1$ is hydrogen or lower alkyl of 1–3 carbons, $R^2$ is carboxyl, hydroxymethyl, lower alkanoyloxymethyl, or lower alkoxycarbonyl, $R^3$ is hydrogen, lower alkyl or benzyl, and $R^4$ and $R^5$ are the same or different and represent hydrogen, lower alkyl, lower alkoxy, alkanoyloxy, benzyloxy, hydroxy, halogen (Cl, Br and F), nitro, and trifluoromethyl. These compounds are useful as anti-allergics when administered parenterally or by insufflation but have poor activity when administered orally.

8 Claims, No Drawings

THIOXOPYRAZOLO[1,5-C]QUINAZOLINE DERIVATIVES, ANTI-ALLERGIC COMPOSITIONS AND METHODS FOR TREATING ALLERGIC CONDITIONS BY PARENTERAL ADMINISTRATION, AEROSOL OR INSUFFLATION

REFERENCE TO OTHER APPLICATIONS

This application is a continuation-in-part of application Ser. No. 900,050, filed Apr. 26, 1978, now abandoned.

DESCRIPTION OF THE INVENTION

The present invention relates to thioxopyrazolo-[1,5-c]quinazoline derivatives of the structure

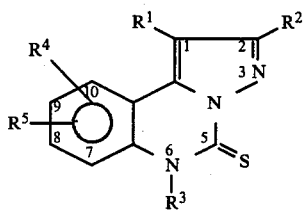

wherein $R^1$ represents hydrogen or lower alkyl, $R^2$ is carboxyl, hydroxymethyl, lower alkanoyloxymethyl, or lower alkoxycarbonyl, $R^3$ is hydrogen, lower alkyl or benzyl, $R^4$ and $R^5$ may be the same or different and are hydrogen, lower alkyl (1–4 carbons), lower alkoxy (1–4 carbons), hydroxy, alkanoyloxy (1–4 carbons), nitro, trifluoromethyl, halogen or

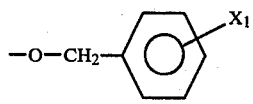

($X_1$ is hydrogen, lower alkoxy (1–4 carbons), Cl, F, Br, $CF_3$ or $NO_2$).

Preferred are those compounds of Formula I wherein $R^2$ is carboxyl or lower alkoxycarbonyl, $R^1$ is hydrogen, $R^3$ is hydrogen, $R^4$ and $R^5$ are hydrogen.

Unless otherwise indicated the term "lower alkyl" or "alkyl" as employed herein includes both straight and branched chain radicals of up to eight carbon atoms, for instance, methyl, ethyl, n-propyl, isopropyl, n-butyl, t-butyl, isobutyl, n-pentyl, n-hexyl, isohexyl, n-heptyl, 4,4-dimethylpentyl, n-octyl, 2,2,4-trimethylpentyl, and the like.

Unless otherwise indicated, the term "lower alkoxy" or "alkoxy" includes straight and branched chain radicals which correspond to the above lower alkyl groups attached to an oxygen atom.

Unless otherwise indicated, the term "lower alkanoyl" or "alkanoyl" as employed herein includes any of the above lower alkyl groups linked to a carbonyl group.

The compounds of Formula I of the invention may be prepared by several methods.

One method involves preparation of compounds of the structure

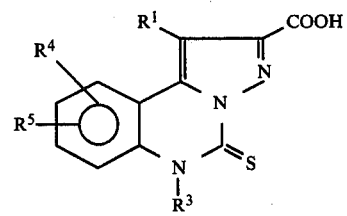

wherein $R^1$, $R^3$, $R^4$ and $R^5$ are as defined hereinbefore. The Formula II compounds are prepared by reacting compounds of the structure

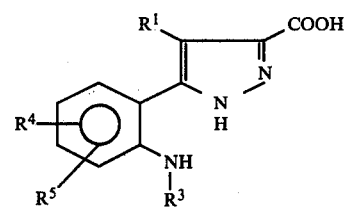

with carbon disulfide in the presence of a base, such as alkali metal hydroxide, alkaline earth metal hydroxide or quaternary ammonium hydroxide or a heterocyclic amine, such as pyridine, preferably at reflux under nitrogen for periods of 1 to 48 hours.

The Formula III compounds may be prepared as described in U.S. Pat. No. 3,895,027 to Katner.

The Formula II acid compounds of the invention may be employed to prepare the ester compounds of Formula IV of the invention, namely,

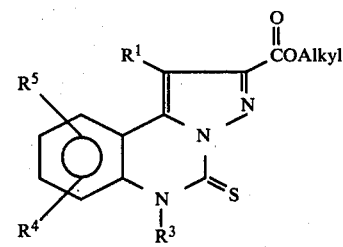

by reacting the Formula II acid with phosphorus pentachloride in the presence of an inert solvent, such as halogenated hydrocarbons, for example, methylene chloride, chloroform or trichloroethylene to form the intermediate acid chloride

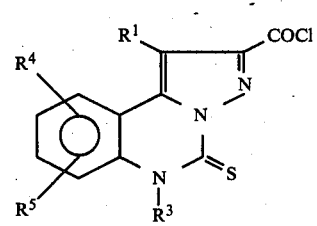

The acid chloride V is reacted with a lower alkanol (alkyl—OH) at reflux under nitrogen for 1 to 4 hours to form the Formula IV esters.

The Formula IV esters may also be prepared from the corresponding ester analog of Formula VI (disclosed in U.S. Pat. No. 3,897,434 to Katner).

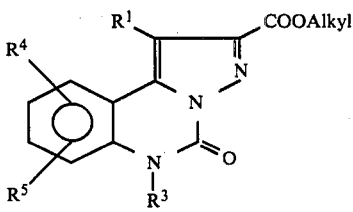

The Formula VI esters are reacted with phosphorus pentasulfide in the presence of a base, such as pyridine or an inorganic alkali metal or alkaline earth metal hydroxide as set out hereinbefore, preferably under an inert atmosphere, for periods ranging from 0.5 to 48 hours to form the Formula IV esters of the invention.

The Formula IV esters may be employed in preparing the corresponding hydroxyl derivatives of Formula VII

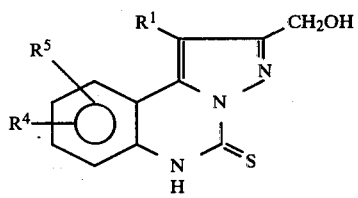

by reducing the Formula IV esters with metal hydrides, such as aluminum hydride; substituted metal hydrides, such as diisobutyl aluminum hydride; complex metal hydrides, such as magnesium aluminum hydride, sodium aluminum hydride, aluminum borohydride, sodium borohydride, lithium borohydride, calcium borohydride and the like, alkoxyaluminum hydrides, such as sodium di-(2-methoxyethoxy)aluminum hydride and the like.

The reaction can be run in inert non-hydroxylic organic solvents, such as ether (4–12 carbons), for example, diethyl ether, diisopropyl ether, diphenyl ether, tetrahydrofuran, dioxane, 1,2-dimethoxyethane and the like; saturated hydrocarbons (6–10 carbons), such as n-hexane, cyclohexane; aromatic hydrocarbons (6–10 carbons), such as benzene, toluene, xylene; halogenated hydrocarbons (1–4 carbons), such as methylene chloride, chloroform, dichloroethane, tetrachloroethane; or, where compatible with the less reactive reducing agents, such as sodium borohydride, in alkanols (1–6 carbons) such as methanol, isopropanol or, preferably, ethanol, at a temperature of 25° C. to reflux for 0.5 hour to 48 hours.

Compounds of Formula VIII of the invention

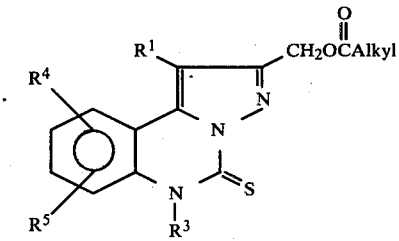

may be prepared by reacting compounds of Formula VII with a lower alkanoic acid under an inert atmosphere preferably at reflux temperature.

Certain of the compounds of Formula I may form physiologically acceptable acid-addition salts or base addition salts with inorganic and organic acids or alkali metal or alkaline earth metal bases such as sodium bicarbonate, sodium hydroxide or calcium hydroxide. These salts frequently provide useful means for isolating the products from reaction mixtures by forming the salt in a medium in which it is insoluble. The free base may then be obtained by neutralization, e.g., with a base or acid. Then any other salt may again be formed from the free base and the appropriate inorganic acid or base. Illustrative are the hydrohalides, especially the hydrochloride and hydrobromide which are preferred, sulfate, nitrate, phosphate, oxalate, tartrate, maleate, fumarate, citrate, succinate, methane-sulfonate, benzenesulfonate, toluenesulfonate, and the like.

The compounds of Formula I, and their pharmaceutically acceptable salts, are useful in treating various allergic conditions in mammalian species such as mice, cats, dogs, etc., when administered in amounts ranging from about 1 milligram to about 500 milligrams per kilogram of body weight per day. The compounds can be used prophylactically or therapeutically to treat various allergic and immunological disorders and in particular to treat certain types of asthma, hay-fever, and rhinitis. A preferred dosage regimen would be from about 3 milligrams to about 200 milligrams per kilogram of body weight per day administered in a single dose or plurality of divided doses.

The compounds of Formula I, and the pharmaceutically acceptable salts thereof, are anti-allergics which inhibit the effects of certain antigen-antibody reactions and in particular inhibit the release of mediators such as histamine. The anti-allergy activity of these compounds is determined by the reaginic antibody induced passive cutaneous anaphylaxis (PCA) reaction in rats. (See Bach, Immediate Hypersensitivity: Laboratory Models and Experimental Findings, Ann. Rep. Med. Chem., 7:238–248 (1972), for a discussion of the predictability of clinical efficacy of compounds active in the PCA).

A compound of Formula I, or a salt thereof, can be administered by the inhalation of an aerosol or powder as described in U.S. Pat. No. 3,772,336 (i.e., breathing finely divided particles of the active ingredient into the lungs), or parenterally, such as interperitoneally.

A suitable form for parenteral administration is a sterile injectable. Such unit dosage forms are prepared by compounding with a conventional vehicle, excipients, or the like as called for by acceptable pharmaceutical practice. Also, the compounds of this invention can be formulated with other pharmaceutically active compounds such as bronchodilators, steroids, antihistamines, etc.

Furthermore, the compounds of the invention are useful in mammals as inhibitors of 3',5'-cyclic adenosine phosphodiesterase and 3',5'-cyclic guanosine phosphodiesterase and as inhibitors of platelet aggregation in vitro and therefore of potential use in the treatment of thrombosis.

The compounds of the present invention in the described dosages may be administered intraperitoneally, subcutaneously, intramuscularly or intravenously. They have little or no activity when administered perorally. Accordingly, the compounds of the invention may be administered by aerosol or insufflation for the treatment of allergic diseases without the concern for the effects produced on oral administration, such as stomach distress and the like.

The following Examples further illustrate and represent preferred embodiments of the invention. All temperatures are expressed in degrees Centigrade.

The letter "(d)" following a melting point indicates at least some apparent decomposition was observed. The term "stripped" also means evaporation.

EXAMPLE 1

5,6-Dihydro-5-thioxopyrazolo[1,5-c]quinazoline-2-carboxylic acid

A mixture of 600 mg (0.0025 mole) of 5-(2-aminophenyl)-1H-pyrazole-3-carboxylic acid hydrochloride, 1.98 ml of carbon disulfide, 3.2 ml of pyridine and 0.16 ml of water are refluxed under $N_2$ for 40 hours. The reaction mixture is stripped to dryness and the solid obtained is taken up in 175 ml methanol and filtered while hot. The clear light-yellow filtrate is concentrated down to a volume of 80 ml and cooled. The cotton-like precipitates are filtered and dried in vacuo over a 72 hour period at 80°. Yield: 394.8 mg, m.p. 272°–273°, 64.4% recryst. yield.

EXAMPLE 2

5,6-Dihydro-5-thioxopyrazolo[1,5-c]quinazoline-2-carboxylic acid, ethyl ester 1.5 g (0.006 mole) of 5,6-dihydro-5-thioxopyrazolo-[1,5-c]quinazoline-2-carboxylic acid (prepared as described in Example 1) and 1.26 g (1 equivalent) of phosphorus pentachloride are heated together in 50 ml of methylene chloride at 60° for 30 minutes. The reaction mixture is cooled and the solvent stripped off and replaced with 50 ml of dry pyridine. The solution is treated with 1.1 ml of absolute ethanol and refluxed under $N_2$ for 2 hours.

The reaction mixture is stripped to dryness and the solid obtained is evaporated once from benzene. The crude mixture is then taken up in a mixture of methanol (100 ml) and chloroform (75 ml) and impregnated onto silica gel. The product is chromatographed on a silica gel column (45 g), eluting the column successively with methylene chloride (150 ml) and $CH_2Cl_2$:EtOAc (8:2, 1.0 l.). The fractions containing the desired product are combined to give 900 mg of the product plus a trace of an impurity at the solvent front. Percent yield from column=54.9% (theor.—1.64 g).

The material obtained from the column is recrystallized from benzene (25 ml) and the precipitates obtained are dried overnight in vacuo at 100°. Yield: 617 mg, m.p. 258°–259°.

EXAMPLE 3

5,6-Dihydro-5-thioxopyrazolo[1,5-c]quinazoline-2-carboxylic acid, ethyl ester 5.9 g (2.3 mmole) of 5,6-dihydro-5-oxopyrazolo-[1,5-c]quinazoline-2-carboxylic acid, ethyl ester and 13.1 g (2.6 equivalents) of $P_2S_5$ are refluxed in pyridine (650 ml) under nitrogen for 19 hours. The reaction mixture is cooled down to room temperature and the precipitates that form are filtered off and washed with pyridine. The clear filtrate and washings are then poured onto 700 ml ice-water, stirred for 30 minutes and the precipitates that form are filtered off. The precipitates are taken up in 1 l. of $CH_3OH$:$CHCl_3$ (1:1) and the solution is stripped to dryness. Yield: 10.0 g of an amorphous reddish solid. The crude product is impregnated onto silica gel and chromatographed on a silica gel column (250 g), eluting the column successively with $CHCl_3$ (250 ml) and $CHCl_3$:$CH_3OH$ (9:1, 1.5 l.). The first 650 ml collected is discarded and the next 600 ml containing a mixture of the starting material and desired product is collected and stripped to dryness. Yield: 4.5 g.

800 mg of the crude mixture is taken up in 20 ml of $CH_2Cl_2$:$CH_3OH$ (1:1) and applied to 5 preparative silica gel plates. The plates are eluted with $CHCl_3$:EtOAc (6:4) and the desired band extracted with three 150 ml portions of $CH_2Cl_2$.$CH_3OH$ (5:1). The extracts are evaporated down to give 350 mg of the desired product. Recrystallization from EtOAc (25 ml) gives two crops: 110.3 mg, m.p. 242°–243°; 73.5 mg, m.p. 243°–244°. Both crops are single spots with Rf 0.6 (silica gel; $CHCl_3$:EtOAc—6:4).

EXAMPLE 4

5,6-Dihydro-5-thioxopyrazolo[1,5-c]quinazoline-2-carboxylic acid, sodium salt 1.5 g (0.006 mole) of 5,6-dihydro-5-thioxopyrazolo-[1,5-c]quinazoline-2-carboxylic acid (prepared as described in Example 1) is suspended in 150 ml of water, treated with 513.8 mg of sodium bicarbonate (1 equivalent) and stirred overnight at room temperature. The insoluble precipitates are filtered off and the clear filtrate stripped to dryness. The solid obtained is triturated with 12 ml of 50% aqueous methanol and filtered, washing the precipitates with a small amount of aqueous methanol. The product is dried in vacuo over $P_2O_5$ for 5 hours at 100° and then overnight at 80° (without $P_2O_5$). Yield: 1.35 g, m.p. >350° dec. Percent yield: 82.8% (theor. yield=1.63 g).

EXAMPLE 5

2-(Hydroxymethyl)pyrazolo[1,5-c]quinazoline-5(6H)-thione 1.37 g (0.005 mole) of 5,6-dihydro-5-thioxopyrazolo-[1,5-c]quinazoline-2-carboxylic acid ethyl ester prepared as described in Example 2 is suspended in 100 ml of dichloromethane and treated with 8 ml (0.011 mole) of 20% diisobutylaluminum hydride (Dibal). The resultant yellow solution is stirred at room temperature for 45 minutes, 2.0 ml (0.003 M) of Dibal solution is added and stirring continued for 17 hours.

An additional 2.0 ml (0.003 mole) of Dibal solution is added and the reaction stirred for 2 hours (total reaction time 20 hours). The reaction mixture is stripped to an oil, triturated and suspended in 1 N hydrochloric acid. The solid is filtered off and dried to give the product.

EXAMPLE 6

2-[(Acetyloxy)methyl]pyrazolo[1,5-c]quinazoline-5(6H)-thione 3.23 g (0.014 mole) of the product of Example 5 [2-(hydroxymethyl)pyrazolo[1,5-c]quinazoline-5(6H)-thione] is refluxed with 250 ml of glacial acetic acid for 20 hours under nitrogen. The solution is cooled and stripped to a solid residue which is dissolved in a mixture of ethyl acetate-absolute ethanol. The volume of solution is reduced and the concentrated solution set aside at 5°. The precipitate is filtered off to give the product. Recrystallization from ethyl acetate-absolute ethanol gives the title compound.

EXAMPLES 7 TO 25

Following the procedure of Example 1, except substituting the compounds indicated in Column I of Table I set out below for 5-(2-aminophenyl)-1H-pyrazole-3-carboxylic acid hydrochloride, the compounds indicated in Column II are obtained.

set out below for 5,6-dihydro-5-thioxopyrazolo-[1,5-c]quinazoline-2-carboxylic acid, and substituting for ethanol, the alcohols set out in Column II, the compounds indicated in Column III are obtained.

TABLE I

| Ex. No. | Column I R$^4$ (position) | R$^5$ (position) | R$^3$ | Column II R$^4$ (position) | R$^5$ (position) | R$^3$ |
|---|---|---|---|---|---|---|
| 7. | H | H | H | H | as per Column I | as per Column I |
| 8. | H | H | CH$_3$ | H | | |
| 9. | CH$_3$O(3) | H | H | CH$_3$O(7) | | |
| 10. | CH$_3$O(4) | H | H | CH$_3$O(8) | | |
| 11. | C$_2$H$_5$O(4) | H | C$_2$H$_5$ | C$_2$H$_5$O(8) | | |
| 12. | CH$_3$O(5) | H | H | CH$_3$O(9) | | |
| 13. | CH$_3$O(6) | H | H | CH$_3$O(10) | | |
| 14. | CH$_3$O(6) | H | CH$_3$ | CH$_3$O(10) | | |
| 15. | n-C$_3$H$_7$O(6) | H | H | n-C$_3$H$_7$O(10) | | |
| 16. | CH$_3$O(6) | H | CH$_2$C$_6$H$_5$ | CH$_3$O(10) | | |
| 17. | CH$_3$O(5) | H | H | CH$_3$O(9) | | |
| 18. | i-C$_4$H$_9$(4) | H | H | i-C$_4$H$_9$(8) | | |
| 19. | CH$_3$(6) | H | CH$_3$ | CH$_3$(10) | | |
| 20. | CH$_3$(5) | H | H | CH$_3$(9) | | |
| 21. | F(5) | H | C$_2$H$_5$ | F(9) | | |
| 22. | Cl(6) | CH$_3$O(3) | n-C$_3$H$_7$ | Cl(10) | CH$_3$O(7) | |
| 23. | CF$_3$(3) | H | CH$_2$C$_6$H$_5$ | CF$_3$(7) | | |
| 24. | C$_6$H$_5$—CH$_2$O(6) | H | H | C$_6$H$_5$—CH$_2$O(10) | | |
| 25. | CH$_3$CO(5) (O=) | H | H | CH$_3$CO(9) (O=) | | |

EXAMPLES 26 TO 44

Following the procedure of Example 2, except substituting the compounds indicated in Column I of Table II

TABLE II

| Ex. No. | Column I R$^4$ (position) | R$^5$ (position) | R$^3$ | Column II Alkyl | Column III R$^4$ (position) | R$^5$ (position) | R$^3$ | Alkyl |
|---|---|---|---|---|---|---|---|---|
| 26. | H | H | H | CH$_3$ | as per Column I | | | as per Column II |
| 27. | H | H | H | C$_2$H$_5$ | | | | |
| 28. | CH$_3$O(7) | H | H | n-C$_3$H$_7$ | | | | |
| 29. | CH$_3$O(8) | H | H | CH$_3$ | | | | |
| 30. | C$_2$H$_5$O(8) | H | C$_2$H$_5$ | C$_2$H$_5$ | | | | |
| 31. | CH$_3$O(9) | H | H | n-C$_3$H$_7$ | | | | |
| 32. | CH$_3$O(10) | H | H | CH$_3$ | | | | |
| 33. | CH$_3$O(10) | H | CH$_3$ | C$_2$H$_5$ | | | | |
| 34. | n-C$_3$H$_7$O(10) | H | H | n-C$_8$H$_{17}$ | | | | |
| 35. | CH$_3$O(10) | H | CH$_2$C$_6$H$_5$ | CH$_3$ | | | | |
| 36. | CH$_3$O(9) | H | H | C$_2$H$_5$ | | | | |
| 37. | i-C$_4$H$_9$(8) | H | H | i-C$_3$H$_7$ | | | | |
| 38. | CH$_3$(10) | H | CH$_3$ | CH$_3$ | | | | |
| 39. | CH$_3$(9) | H | H | C$_2$H$_5$ | | | | |
| 40. | F(9) | H | C$_2$H$_5$ | n-C$_3$H$_7$ | | | | |
| 41. | Cl(10) | CH$_3$O(3) | n-C$_3$H$_7$ | CH$_3$ | | | | |
| 42. | CF$_3$(7) | H | CH$_2$C$_6$H$_5$ | C$_2$H$_5$ | | | | |

TABLE II-continued

| | Column I | | | Column II | Column III | | |
|---|---|---|---|---|---|---|---|
| Ex. No. | $R^4$ (position) | $R^5$ (position) | $R^3$ | Alkyl | $R^4$ (position) | $R^5$ (position) | $R^3$ | Alkyl |
| 43. | C₆H₅-CH₂O(10) | H | H | n-C₅H₁₁ | | | | |
| 44. | CH₃CO(9) (O=) | H | H | CH₃ | | | | |

EXAMPLES 45 TO 63

Following the procedure of Example 5 or Example 83, except substituting the compounds indicated in Column I of Table III set out below for 5,6-dihydro-5-thioxopyrazolo-[1,5-c]quinazoline-2-carboxylic acid ethyl ester, the compounds indicated in Column II are obtained.

EXAMPLES 64 TO 82

Following the procedures of Example 6, except substituting the compounds indicated in Column I of Table IV set out below for 2-(hydroxymethyl)pyrazolo-[1,5-c]quinazoline-5(6H)-thione, and substituting for acetic acid, the acid indicated in Column II, the compounds indicated in Column III are obtained.

TABLE III

| | Column I | | | | Column II | | |
|---|---|---|---|---|---|---|---|
| Ex. No. | Alkyl | $R^4$ (position) | $R^5$ (position) | $R^3$ | $R^4$ (position) | $R^5$ (position) | $R^3$ |
| 45. | CH₃ | H | H | H | as per Column I | | |
| 46. | C₂H₅ | H | H | CH₃ | | | |
| 47. | n-C₃H₇ | CH₃O(7) | H | H | | | |
| 48. | CH₃ | CH₃O(8) | H | H | | | |
| 49. | C₂H₅ | C₂H₅O(8) | H | C₂H₅ | | | |
| 50. | n-C₃H₇ | CH₃O(9) | H | H | | | |
| 51. | CH₃ | CH₃O(10) | H | H | | | |
| 52. | C₂H₅ | CH₃O(10) | H | CH₃ | | | |
| 53. | n-C₈H₁₇ | C₃H₇O(10) | H | H | | | |
| 54. | CH₃ | CH₃O(10) | H | CH₂C₆H₅ | | | |
| 55. | C₂H₅ | CH₃O(9) | H | H | | | |
| 56. | i-C₃H₇ | i-C₄H₉(8) | H | H | | | |
| 57. | CH₃ | CH₃(10) | H | CH₃ | | | |
| 58. | C₂H₅ | CH₃(9) | H | H | | | |
| 59. | n-C₃H₇ | F(9) | H | C₂H₅ | | | |
| 60. | CH₃ | Cl(10) | CH₃O(7) | C₃H₇ | | | |
| 61. | C₂H₅ | CF₃(7) | H | CH₂C₆H₅ | | | |
| 62. | n-C₅H₁₁ | C₆H₅-CH₂O(10) | H | H | | | |
| 63. | CH₃ | CH₃CO(5) (O=) | H | H | | | |

TABLE IV

| | Column I 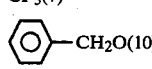 | | | | Column II | Column III  | | |
|---|---|---|---|---|---|---|---|---|
| Ex. No. | R⁴ (position) | R⁵ (position) | R³ | Alkyl | AlkylCOOH Alkyl | R⁴ (position) | R⁵ (position) | R³ Alkyl |
| 64. | H | H | H | $CH_3$ | | as per Column I | | as per Column II |
| 65. | H | H | $CH_3$ | $C_2H_5$ | | | | |
| 66. | $CH_3O(7)$ | H | H | $n$-$C_3H_7$ | | | | |
| 67. | $CH_3O(8)$ | H | H | $CH_3$ | | | | |
| 68. | $C_2H_5O(8)$ | H | $C_2H_5$ | $C_2H_5$ | | | | |
| 69. | $CH_3O(9)$ | H | H | $n$-$C_3H_7$ | | | | |
| 70. | $CH_3O(10)$ | H | H | $CH_3$ | | | | |
| 71. | $CH_3O(10)$ | H | $CH_3$ | $C_2H_5$ | | | | |
| 72. | $n$-$C_3H_7O(10)$ | H | H | $i$-$C_3H_7$ | | | | |
| 73. | $CH_3O(10)$ | H | $CH_2C_6H_5$ | $CH_3$ | | | | |
| 74. | $CH_3O(9)$ | H | H | $C_2H_5$ | | | | |
| 75. | $i$-$C_4H_9(8)$ | H | H | $n$-$C_3H_7$ | | | | |
| 76. | $CH_3(10)$ | H | $CH_3$ | $CH_3$ | | | | |
| 77. | $CH_3(9)$ | H | H | $C_2H_5$ | | | | |
| 78. | F(9) | H | $C_2H_5$ | $n$-$C_3H_7$ | | | | |
| 79. | Cl(10) | $CH_3O(3)$ | $n$-$C_3H_7$ | $CH_3$ | | | | |
| 80. | $CF_3(7)$ | H | $CH_2C_6H_5$ | $C_2H_5$ | | | | |
| 81. | C₆H₅—$CH_2O(10)$ | H | H | $n$-$C_3H_7$ | | | | |
| 82. | $CH_3CO(9)$ (O=) | H | H | $CH_3$ | | | | |

EXAMPLE 83

2-(Hydroxymethyl)pyrazolo[1,5-c]quinazoline-5(6H)-thione 0.519 g (0.0019 mole) of 5,6-dihydro-5-thioxopyrazolo-[1,5-c]quinazoline-2-carboxylic acid ethyl ester is suspended in 10 ml distilled tetrahydrofuran and treated with 0.1 g (0.004 mole) of 85% lithium borohydride at room temperature. After 20 hours of stirring, the reaction mixture is cooled to 0°, 4.5 ml of 1N hydrochloric acid is added and stirring is continued for 30 minutes. 25 ml of water is added and the product is filtered off after 10 minutes and dried.

EXAMPLE 84

The following experiment is carried out to determine the anti-allergy activity of 5,6-dihydro-5-thioxopyrazolo-[1,5-c]quinazoline-2-carboxylic acid, sodium salt (one of the compounds of the invention) and its corresponding oxo analog, that is, 5,6-dihydro-5-oxopyrazolo[1,5-c]quinazoline-2-carboxylic acid, sodium salt.

The rat IgE (reaginic antibody) mediated rat passive cutaneous anaphylaxis (PCA) reaction is used as a screen to determine if the test compounds 5,6-dihydro-5-thioxopyrazolo-[1,5-c]quinazoline-2-carboxylic acid, sodium salt and 5,6-dihydro-5-oxopyrazolo[1,5-c]quinazoline-2-carboxylic acid, sodium salt are active as anti-allergy agents. In this test, 0.05 ml of appropriately diluted whole rat serum containing IgE antibody is injected intradermally into the skin of a rat. The next day, the animals are dosed with the test compound 10 minutes prior to the intravenous challenge of antigen and Evan's blue dye. Thirty minutes later, the animals are sacrificed, the skin reflected and the reaction quantitated by measuring the dye marked edema and scoring the color intensity of the reaction.

The activity of 5,6-dihydro-5-thioxopyrazolo[1,5-c]-quinazoline-2-carboxylic acid, sodium salt is compared with the activity of 5,6-dihydro-5-oxopyrazolo[1,5-c]quinazoline-2-carboxylic acid, sodium salt in this rat IgE-mediated passive cutaneous anaphylaxis reaction. The % inhibition of edema and the dose in mg/kg producing such inhibition of edema for the above compounds, were determined. The results obtained are tabulated below.

| Test Compound | Route | Dose mg/kg | % Inhibiton |
|---|---|---|---|
| 1. 5,6-dihydro-5-thioxopyrazolo-[1,5-c]quinazoline-2-carboxylic acid, sodium salt (compound of the invention) | po<br>ip | 75<br>75 | 28<br>82 |
| 2. 5,6-dihydro-5-oxopyrazolo-[1,5-c]quinazoline-2-carboxylic acid, sodium salt (prior art compound) | po<br>ip | 75<br>not tested | 99 | po = peroral
ip = interperitoneal

The above results demonstrate that 5,6-dihydro-5-thioxopyrazolo[1,5-c]quinazoline-2-carboxylic acid, sodium salt possesses the advantage of being active ip (interperitoneal) in the passive cutaneous anaphylaxis (PCA) test with little or no activity on oral administration. Thus, unlike the oxygen analog, 5,6-dihydro-5-oxopyrazolo-[1,5-c]quinazoline-2-carboxylic acid, sodium salt, which possesses oral activity in this test, 5,6-dihydro-5-thioxopyrazolo[1,5-c]quinazoline-2-carboxylic acid, sodium salt can be used by aerosol or insufflation administration for the treatment of allergic diseases without concern for the effects produced on oral absorption.

What is claimed is:

1. A compound of the structure

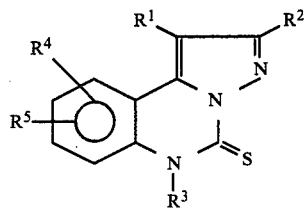

wherein $R^1$ is hydrogen or lower alkyl containing 1 to 8 carbons; $R^2$ is carboxyl or lower alkoxycarbonyl containing 1 to 8 carbons in the alkoxy group; $R^3$ is hydrogen, lower alkyl containing 1 to 8 carbons or benzyl; $R^4$ and $R^5$ are the same or different and are selected from the group consisting of hydrogen, alkyl of 1 to 4 carbons, alkoxy of 1 to 4 carbons, lower alkanoyloxy of 1 to 4 carbons, nitro, halogen, trifluoromethyl, benzyloxy, benzyloxy having a lower alkoxy containing 1 to 8 carbons, halogen, hydroxy, or trifluoromethyl substituent, with the proviso that where $R^4$ and $R^5$ are alkyl at least one of $R^4$ and $R^5$ is other than t-butyl; and physiologically acceptable salts thereof.

2. The compound of claim 1 wherein $R^2$ is carboxyl.

3. The compound of claim 1 wherein $R^2$ is lower alkoxycarbonyl.

4. The compound of claim 1 having the name 5,6-dihydro-5-thioxopyrazolo[1,5-c]quinazoline-2-carboxylic acid.

5. The compound of claim 1 having the name 5,6-dihydro-5-thioxopyrazolo[1,5-c]quinazoline-2-carboxylic acid, ethyl ester.

6. The compound of claim 1 having the name 5,6-dihydro-5-thioxopyrazolo[1,5-c]quinazoline-2-carboxylic acid, sodium salt.

7. A pharmaceutical composition for use in treating allergic conditions and adapted for administration parenterally, by aerosol or by insufflation, consisting essentially of a compound as defined in claim 1 and a pharmaceutically acceptable parenteral, aerosol or insufflation carrier therefor.

8. A method for treating allergic conditions in mammals, which includes the step of administering to the mammalian host by parenteral administration, aerosol or insufflation a therapeutic amount of a compound as defined in claim 1.

* * * * *